Figure 1:
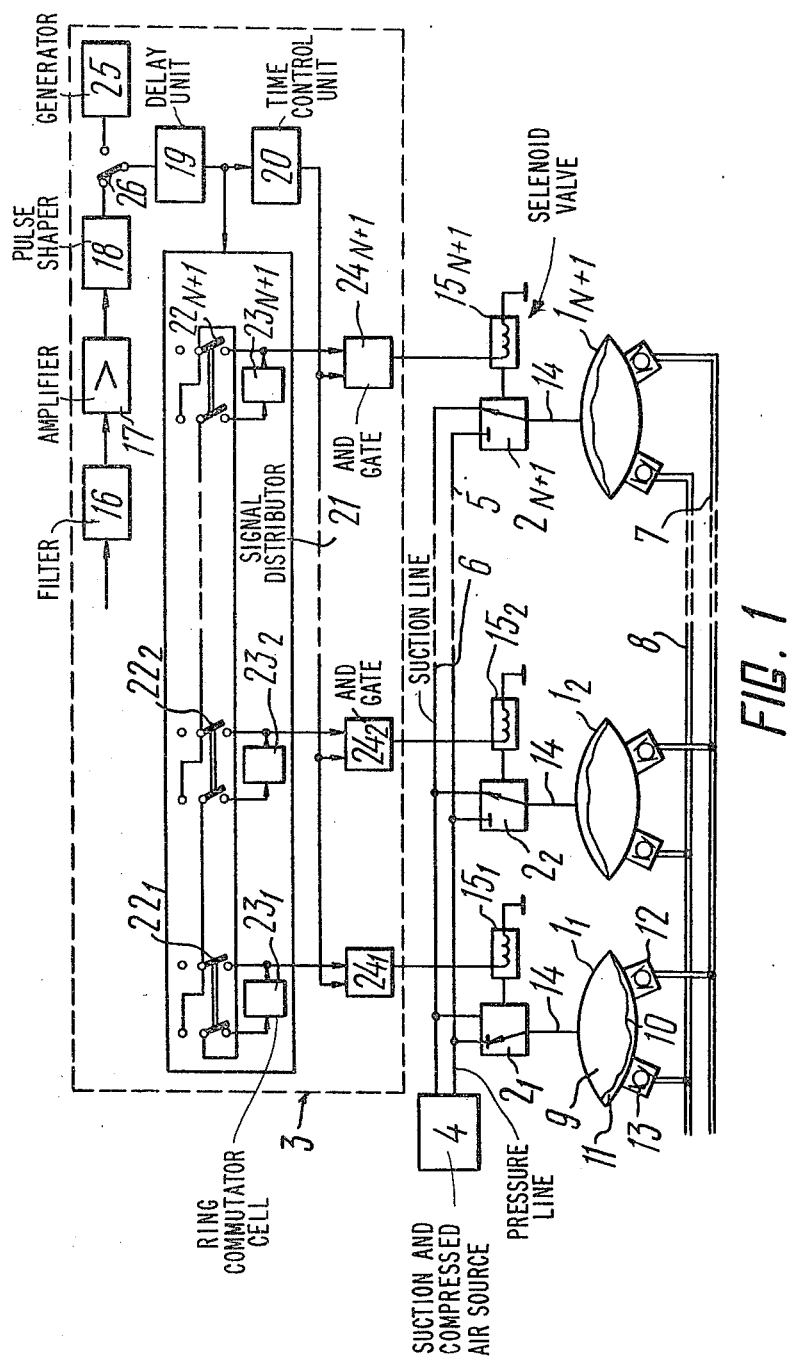

United States Patent [19]

Chazov et al.

[11] 4,135,496
[45] Jan. 23, 1979

[54] EXTRACORPOREAL CIRCULATION APPARATUS

[75] Inventors: Evgeny I. Chazov; Mikhail Y. Ruda; Vitaly A. Burynin; Moisei A. Lokshin, all of Moscow, U.S.S.R.

[73] Assignee: Institut Kardiologii Imeni A.L. Myasnikova Akademii Meditsinskikh Nauk SSSR, U.S.S.R.

[21] Appl. No.: 653,714

[22] Filed: Jan. 30, 1976

[51] Int. Cl.² ............................................. A61M 1/03
[52] U.S. Cl. .............................. 128/1 D; 128/2.06 R; 3/1.7
[58] Field of Search ............. 128/1 D, DIG. 3; 3/1.7

[56] References Cited

U.S. PATENT DOCUMENTS

| | | | |
|---|---|---|---|
| 3,426,743 | 2/1969 | Chestnut et al. | 128/1 D |
| 3,430,624 | 3/1969 | Flanagan et al. | 128/1 D |
| 3,572,979 | 3/1971 | Morton | 128/1 D X |
| 3,791,374 | 2/1974 | Guarino | 128/1 D |
| 3,955,557 | 5/1976 | Takagi | 128/1 D |

FOREIGN PATENT DOCUMENTS 303078  7/1971  U.S.S.R. .................................. 128/1 D

Primary Examiner—Kyle L. Howell
Attorney, Agent, or Firm—Steinberg & Blake

[57] ABSTRACT

The extracorporeal circulation apparatus in accordance with the invention comprises a plurality of pneumatic diaphragm pumps incorporated in parallel relationship in a single fluid-flow system of extracorporeal blood perfusion.

The electronic control system of the arrangement which processes the EKG signals is provided with a control signal distributor for sequential pump actuation such that the priming time of each pump is prolonged, frothing and haemolysis of the blood is prevented, and the stroke volume of the apparatus is maintained at a predetermined level.

3 Claims, 11 Drawing Figures

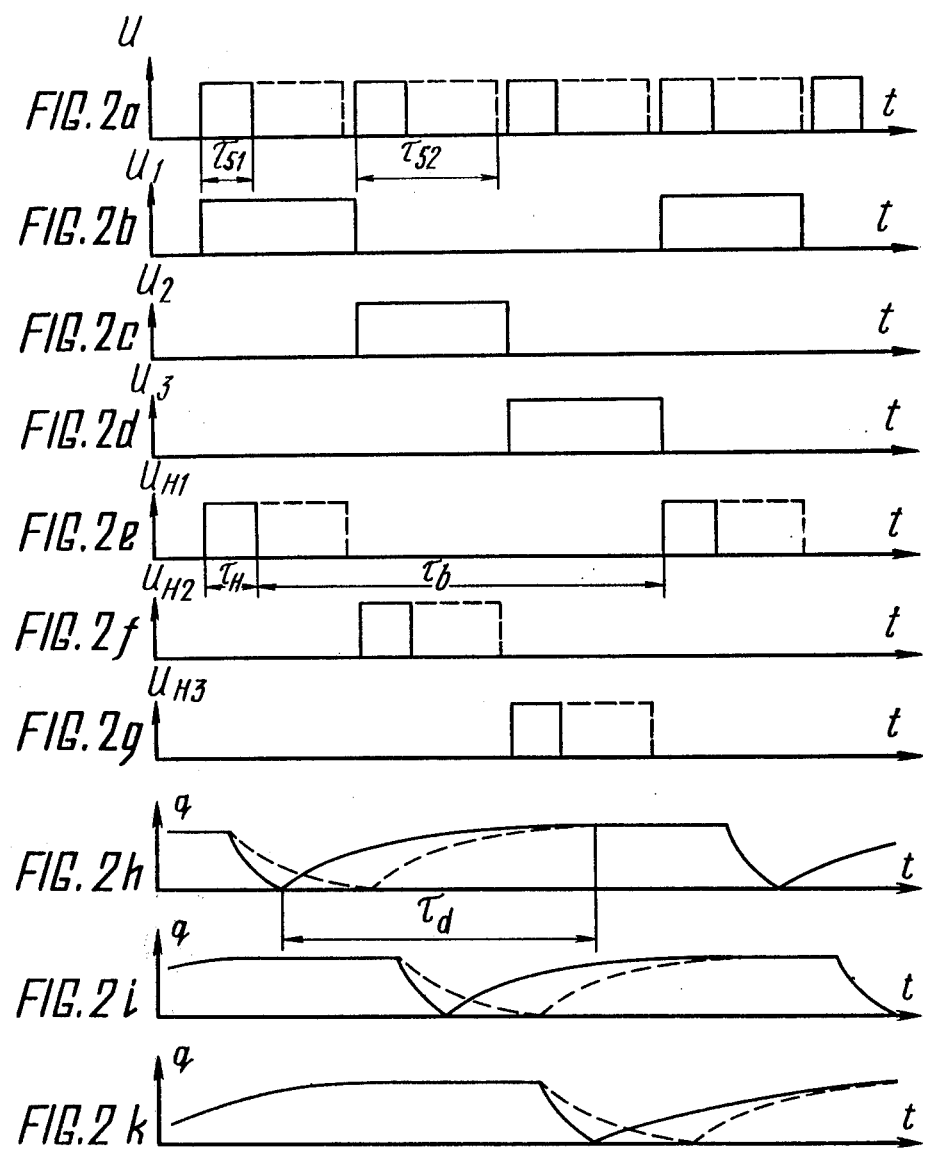

EXTRACORPOREAL CIRCULATION APPARATUS

The present invention relates to medicine and, more particularly, to extracorporeal circulation devices.

It is known in the art to employ extracorporal circulation arrangements, which comprise a blood pump equipped with a suction valve and delivery valves, said pump being incorporated into a fluid-flow line and connected, via a gas chamber, to a source of compressed air supply by way of an electropneumatic valve operated by an electronic control system, the latter being composed of serially interconnected units, viz. a filter, a signal shaper receiving signals from the electrocardiograph via an amplifier, a delay unit, a delivery phase duration control unit coupled to the winding of the electropneumatic valve, and an adjustable pulse generator (see, for example, USSR Inventor's Certificate No. 303,078, Cl. A61m1/02, 1971).

In such known devices, the stroke volume of the pump decreases as the pulse rate increases the reason for which should be sought in the fact that as the frequency increases, the time available for the suction of blood into the working chamber of the pump decreases and so blood fails to fill the entire chamber volume. The stroke volume may be increased by reducing the pressure in the pump gas chamber with the aid of the compressed air supply source, thereby accelerating the blood suction process. But the lower the pressure in the working chamber, the more damage is done to the blood in the arrangement. Increased haemolysis is particularly noticeable in cases of total perfusion required e.g. in cardiac arrest. Furthermore, high vacuum causes blood frothing, i.e., liberation of the gases dissolved in the blood.

It is an object of the present invention to provide an extracorporeal circulation apparatus such as would maintain a predetermined systolic volume (equivalent to cardiac output) even at an increased pulse rate of the patient.

It is another object of the present invention to provide an extracorporeal circulation apparatus of the foregoing type which would rule out the risk of blood frothing and haemolysis in the course of perfusion.

It is a further object of the present invention to provide an extracorporeal circulation apparatus of the foregoing type which would be simpler in design and cheaper than the prior art devices of a similar kind.

It is still another object of the present invention to provide an extracorporeal circulation apparatus of the foregoing type which would ensure a high level of dependability even in cases of accidental failure of the most vulnerable components thereof.

These and other objects are attained in an extracorporeal circulation apparatus, which comprises a main pneumatic pump for extracorporeal blood perfusion with a suction valve and a delivery valve, said pump being incorporated in a blood-flow line connected to the patient and coupled, via a control gas chamber thereof, to a source of compressed air supply by way of an electropneumatic valve operated by an electronic valve control system, said electronic system being composed of the following serially connected units: a filter, an amplifier, an EKG pulse shaper, a delay unit for shifting the signal relative to the EKG R-wave, a unit for controlling the blood delivery phase duration which power is coupled to the winding of the electropneumatic valve, and an adjustable pulse generator, wherein, in accordance with the invention, the blood-flow line includes, in addition to said main pump and in parallelism therewith, auxiliary pumps provided with their own electropneumatic valves each of which is connected to the respective pump as well as to the common source of compressed air supply, and there is provided a circuit for distibuting the signal furnished by said electronic control circuit so that the electropneumatic valves and the pumps are actuated one at a time, thereby increasing the priming time of each pump.

The foregoing design is instrumental in reducing the time of response of the apparatus and increasing its systolic volume at a high pulse rate. Furthermore, the apparatus reduces, rather than increases, the extent of haemolysis because of the lower vacuum created in the gas chamber of the pump at the instant of suction.

The extent of haemolysis is the greatest in cases of total perfusion which is required where the patient's heart is significantly weakened by the disease or totally arrested. In such a case the entire burden of blood delivery is shifted to the extracorporeal circulation apparatus.

With the extent of haemolysis thus reduced, the time of surgical intervention and the "resting period" of the patient's heart can be prolonged accordingly.

In accordance with one of the possible embodiments of the present invention, the extracorporeal circulation apparatus is characterized in that said signal distribution circuit comprises a signal distributor coupled into the electronic control circuit between said delay unit and said unit controlling the duration of the delivery phase in the entire range of frequencies set by said pulse generator, said signal distributor being coupled in parallel with the input of the delivery time control unit and provided with a switch operating the outputs thereof, and also coupled into the circuit between the delivery time control units and the windings of the electropneumatic valves are gate circuits which allow operation of the electropneumatic valve of a given pump only provided the signals from the distributor and from the delivery time control unit are simultaneously fed to the input thereof.

The foregoing design extends the functional scope of the apparatus and permits studying blood circulation under conditions of both pulsating and fixed-rate flows. The fixed rate of blood flow is ensured by the delivery time control unit, which extends the delivery phase throughout the entire pulse period, and also by the signal distributor.

The foregoing design necessitates a simple and reliable signal distributor to ensure a sequential mode of pump operation.

The design of the distributor and output switches conduces to a simple and quick procedure to vary the number of operating pumps, thereby providing for a step-by-step control of the stroke volume of the apparatus. Within each control step, continuous control is ensured by varying the pressure delivered from the source of compressed air supply.

In accordance with another embodiment of the present invention, the extracorporeal circulation apparatus is characterized in that said gate circuit is formed as a plurality of diode-transistor AND gates whose first inputs are coupled to the output of the delivery time control unit and the second inputs to the outputs of the respective cells of the signal distributor.

The latter design necessitates incorporating into the proposed extracorporeal circulation apparatus gate circuits for the signals from the distributor and the delivery time control unit.

With the gate circuit being built around a diode-transistor cell, it is possible to augment its control function by amplitude amplification of the signal which is required to switch over the electropneumatic valve.

The invention will be further understood from the following detailed description of a preferred emodiment thereof taken in conjunction with the accompanying drawings, wherein:

FIG. 1 is a functional diagram of an extracorporeal circulation apparatus in accordance with the invention; and FIGS. 2a-2k are diagrams of the output signals furnished by the units of the control system of the apparatus in accordance with the invention.

Referring now to the drawings, the proposed extracorporeal circulation apparatus comprises pumps $1_1 \ldots 1_{N+1}$ with electropneumatic valves $2_1 \ldots 2_{N+1}$ which are controlled by an electronic system 3, a source 4 of compressed air supply coupled to the electropneumatic valves by a compressed-gas line 5 and a vacuum line 6, and also comprising a feed line 8 and a discharge line 7. All the pumps are identical and each pump incorporates a gas chamber 9 and a working chamber 10 separated by a diaphragm 11. The working chamber is connected with the feed line 8 via a suction valve 13 and with the discharge line 7 via a delivery valve 12. The gas chamber 9 of each pump is connected with the respective electropneumatic valve via a pipeline 14. Each of the electropneumatic valves 2 is switched by a solenoid 15, the electronic control system 3 feeding signals to the winding thereof. The electronic control system 3 includes a unit 16 for filtering the signal furnished by the electrocardiograph connected to the patient, an amplifier 17, a control pulse shaper 18, a delay unit 19 delaying the control signal with respect to the EKG R-wave, and a unit 20 controlling the duration of the delivery phase.

The signals are communicated so as to ensure that the pumps operate one at a time by a signal distributor 21 formed as a ring commutator and provided with N+1 output switches 22 which switch cells 23 of the signal distributor 21, the outputs thereof being coupled to the inputs of respective diode-transistor AND gates $24_1 \ldots 24_{N+1}$.

In case of cardiac arrest, the pulse rate is furnished by an adjustable frequency generator 25 coupled to the control system 3 via a switch 26.

The proposed extracorporal circulation apparatus is capable of operating in the following modes.

1. The operating mode with a single pump is used at a low pulse rate and also where the required perfusion volume is small enough. The signal from the electrocardiograph connected to the patient is fed to the input of the control system 3 directly into the filter 16 which separates the EKG R-wave and suppresses noise. Then the signal is amplified by the amplifier 17 and shaped to a required amplitude and pulse front slope by the pulse shaper 18. The pulse shaper actuates the biased multivibrator of the delay unit 19 by the leading edge of the pulse. The delay unit 19 permits obtaining a pulse of rectangular shape and predetermined length. The trailing edge of the resultant signal triggers the biased multivibrator of the delivery time control unit 20 and also shapes a signal sent to the signal distributor 21.

In the single-pump operating mode, the switches 22 turn off all the outputs of the ring commutator cells 23 but one which generates a signal and sends it to the diode-transistor AND gate 24 corresponding to the operating pump 1. The second input of said AND gate receives a signal from the delivery time control unit 20 corresponding to the delivery phase duration. If both signals appear at the output of the AND gate, the latter passes a signal to the winding of the solenoid 15 of the electropneumatic valve 21. The valve is thereby switched over, communicating the pipeline 14 with the compressed-gas line 5 through which gas is delivered under pressure to the gas chamber 9 of the pump from the source 4. The diaphragm 11 is deflected, pushing the blood from the working chamber 10 via the delivery valve 12 and into the discharge line 7. As the operation triggered by the signal corresponding to the delivery phase duration is over, the electropneumatic valve is reset, communicating the pipeline 14 with the vacuum line 6. The gas chamber is thereby evacuated, and the diaphragm reverts to its original state, drawing blood into the working chamber from the supply line 8 via the suction valve 13. When the next pulse from the electrocardiograph arrives, the whole cycle is repeated.

Should the pump happen to be in disrepair, it is cut off from the hydraulic lines by clamps. The signal sent to the respective electropneumatic valve from the commutator is suppressed by the output switch. The faulty pump is replaced by one of the standby pumps by removing the clamps isolating said latter pump from the hydraulic lines and coupling the respective electropneumatic valve into the signal distributor circuit via the output switch.

2. The operation of the proposed extracorporeal circulation apparatus in a multiple-pump mode is described in the example of three pumps and clarified by the diagram of the output signals supplied by the units of the electronic control system 3, which is shown in FIG. 2. This mode is employed if the patient shows a heightened pulse rate, the number of pumps being dependent on the perfusion volume required. The required number of pumps selected from the total N+1, e.g. three pumps, are connected to the lines by removing the isolating clamps therefrom. The respective electropneumatic valves are coupled into the signal distributor circuit by the output switches. In the case in question, the distributor 21 commutates the signals arriving at the input thereof over three outputs one at a time.

The signals, shaped, amplified and delayed with respect to the EKG R-wave, are fed to the inputs of the signal distributor 21 and the delivery time control unit 20. The latter forms a signal corresponding to the delivery phase duration sends it in parallel to the inputs of the diode-transistor AND gates. FIG. 2a illustrates (solid lines) the shape of the voltage across the output of the unit 20, where $\tau_{S1}$ is the duration of the delivery phase (systole) and $\tau_d$ is the duration of the diastole. The signal shaped in accordance with the systole duration passes to the winding of the solenoid 15 only through the AND gate which at this instant receives, at the input thereof, the signal from the distributor 21, and since the signals from the distributor 21 are sent one at a time from the first, second and third outputs, the electropneumatic valves of the respective pumps will accordingly communicate with pipelines 14 with the compressed-gas line 5 also one at a time. The electropneumatic valves whose windings receive no signal communicate the pipelines 14 with the vacuum line 6. For the rest, the extracorporal circulation apparatus functions in the same way as in the single-pump mode.

FIGS. 2b–d illustrates the shape of the voltage across the outputs of the signal distributor ($U_{t.1}...U_{out.3}$).

FIGS. 2e–g shows (solid lines) the shape of the voltage across the windings of the electropneumatic valves of the operational pumps ($U_{H1}...U_{H3}$), where $\tau_H$ is the delivery phase time and $\tau_B$ is the suction phase time for each pump.

FIG. 2h is an idealized illustration of the ingress of blood into the discharge line 8 resulting from the stroke discharge $Q_1$ of each pump. The frequency of repetition of the delivery phase of the latter relative to the frequency of the signals fed to the input of the control system is inversely proportional to the number of operational pumps, so that the time allotted to the suction phase ($\tau_B > \tau_d$) is increased.

3. A third operating mode is employed in cases of total cardiac arrest. In such a case the patient's pulse rate is entirely provided by the adjustable frequency generator 25 which is connected to the control system via the switch 26. Total perfusion is achieved by setting the frequency of the generator 25 at a level providing for a full systolic volume, and the delivery phase duration is set by the delivery time control unit to be almost equal to the period of the generator frequency, as shown in FIG. 2 by the broken lines, where $\tau_{S2}$ is the delivery phase time and $Q_2$ is the systolic volume. The perfusion volume required determines the generator frequency as well as the number of operational pumps in the extracorporeal circulation apparatus.

The chief units and elements of the proposed extracorporal circulation apparatus are briefly characterized hereinbelow.

FILTER 16

The Filter 16 is formed as an active filter having a V-shaped characteristic adjusted to the mains frequency. A differential T-section filter built around passive RC elements is coupled between two transistor amplification stages forming a feedback circuit.

AMPLIFIER 17

Since the active filter has a gain K of less than unity and the pulse shaper expends a certain amount of power, thereby detracting from the power of the input signal, a single-stage amplifier 17 functions as a compensatory element.

The delay unit is built around a biased multivibrator; it is triggered by the leading edge of the pulse and generates an electric signal of rectangular shape and controlled length.

DELIVERY TIME CONTROL UNIT 20

The unit 20 controls the time during which the electropneumatic valve stays open, i.e., the time during which the electropneumatic valve communicates the gas chamber of the pump with the compressed-gas line.

The delivery time control unit 20 is formed as a biased multivibrator triggered by the trailing edge of the pulse delayed with respect to the R-wave.

PULSE SHAPER 18

The pulse shaper 18 shapes signals stable in amplitude and length. It is built around a Schmitt trigger circuit and generates short pulses.

GENERATOR 25

The generator 25 is employed for independent operation of the extracorporeal circulation apparatus in the absence of EKG signals; it is built around a multivibrator and comprises two transistors differing in conductivity.

DELAY UNIT 19

The delay unit 19 receives the signal to start building up a positive pressure in the gas chamber of the pump, said signal being delayed with respect to the EKG R-wave.

AND GATE 24

The AND gate 24 is gate-transistor logical circuit with two inputs; it is formed as a combination of a diode AND gate and a transistor key with a common emitter functioning as a current amplifier loaded by the winding of the electropneumatic valve.

SIGNAL DISTRIBUTOR 21

The signal distributor 21 may be built around e.g. switching diodes (dynistors). Each cell of the ring commutator is coupled to the next one via a commutating capacitor. The number of gates is equal to the number of pumps.

We propose constructing an extracorporeal circulation apparatus comprising two pumps. For this reason and to simplify the design, the signal distributor 21 has two outputs; it is built around a trigger with a counter input. The output switch permits of the following operating modes of the pumps:

(a) the pump $1_1$ is operational;
(b) the pump $1_2$ is operational;
(c) the pumps $1_1$ and $1_2$ operate alternately.

PUMPS 1 AND 2

The blood is pumped by means of disposable pumps comprising a group of likewise disposable valves. The pump casing is made of two components pressed from organic glass and glued together, with a silicone-rubber diaphragm being put therebetween. One casing component is provided with a sleeve for connection with the electropneumatic valve, while the other has a sleeve for connection with the pump valves.

The extracorporeal circulation apparatus of this invention is designed for pumping blood into the aorta synchronously with the patient's own heart with a view to relieving the load upon the heart, improving the venous blood flow and sustaining the mechanism of nervous regulation of the vascular tone in terminal state therapy and acute cardiac insufficiency.

The proposed apparatus can be employed for blood delivery with an independent frequency, blood delivery by the counter-pulsation method and also venousarterial blood delivery in synchronism with the patient's EKG.

The proposed apparatus can be advantageously employed in cardiological clinics and resuscitation wards.

The apparatus of this invention can be used for performing extracorporeal perfusion without recourse to donor blood for both infants and adult patients.

What is claimed is:

1. In an extracorporeal circulation apparatus, a plurality of pumps each having a working chamber for receiving and discharging a fluid such as blood and a second, pump-operating chamber adapted to communicate with a source of operating fluid which operates each pump, each pump including a pumping member separating said chambers of each pump from each other and creating suction in said working chamber while increasing the volume thereof and reducing the volume of said second, pump-operating chamber, while discharging from said working chamber a fluid, such as blood, under pressure when decreasing the volume of said working chamber while increasing the volume of said second-pump operating chamber, each of said pumps including a pair of one-way valves both of which communicate with said working chamber of each pump and one of which is an inlet valve for permitting fluid to flow only into said working chamber of each pump while the other is an outlet valve for permitting fluid to flow only out of said working chamber of each pump, a feed line communicating with all of said inlet valves for supplying a fluid such as blood to the working chambers of said pumps when said pumping members thereof move along suction strokes increasing the volume of the working chambers of the pumps while decreasing the volumes of the second, pump-operating chambers thereof, and a discharge line communicating with all of said outlet valves for receiving fluid under pressure from said working chambers when said pumping members execute pressure strokes decreasing the volume of said working chambers and increasing the volume of said second, pump-operating chambers, a plurality of solenoid valves respectively communicating with said second, pump-operating chambers of said pumps, a pressure line communicating with each of said solenoid valves and providing a source of fluid under pressure to be delivered through said solenoid valves to said pumps for driving said pumping members along their pressure strokes, a suction line also communicating with all of said solenoid valves and when communicating therethrough with said pumps advancing said pumping members thereof along suction strokes thereof, said solenoid valves respectively having rest positions communicating with said suction line and operating positions communicating with said pressure line, so that when said solenoid valves are in their rest, non-operating positions, the several pumps are respectively connected therethrough to said suction line to maintain said pumping members at the ends of their suction strokes thus maintaining said working chambers filled with fluid from said feed line to be pumped under pressure out of said working chambers when the pumping members are driven along their pressure strokes, means operatively connected with said solenoid valves for operating them sequentially to place said second, pump-operating chambers of said pumps in a given sequence one after the other, but not simultaneously, in communication with said pressure line, so that while any one pump has its pumping member moving along its pressure stroke the other pumps have in their working chambers a supply of fluid to be pumped out of said working chambers according to said given sequence, whereby a considerable amount of time is available for the suction strokes of said pumping members, an electrocardiograph signal means and an adjustable frequency generator means, and switch means for selectively connecting either said electrocardiograph signal means or said frequency generator means to said means for sequentially operating said solenoid valves, whereby said frequency generator means can be used in the case of total cardiac arrest whereas said electrocardiograph signal means can provide a signal from a patient.

2. The combination of claim 1 and wherein said pumps are diaphragm pumps each of which includes a pumping member in the form of a diaphragm which separates said chambers of each pump from each other.

3. The combination of claim 1 and wherein said means for sequentially operating said solenoid valves includes a plurality of AND gates respectively connected with said solenoid valves, distributor means electrically connected with said gates for sequentially transmitting operating signals thereto, and duration-control means for controlling the duration of the pressure strokes of the pumps, said duration-control means being connected with all of said AND gates for simultaneously transmitting signals thereto so that while each AND gate receives a signal both from said duration-control means and said distributor means the solenoid valve connected thereto will be actuated to connect the pump which is controlled by the latter solenoid valve to said pressure line.

* * * * *